US008395774B2

(12) United States Patent
Afzali et al.

(10) Patent No.: US 8,395,774 B2
(45) Date of Patent: Mar. 12, 2013

(54) GRAPHENE OPTICAL SENSOR

(75) Inventors: Ali Afzali, Ossining, NY (US); Ageeth A. Bol, Yorktown Heights, NY (US); Amal Kasry, White Plains, NY (US); George S. Tulevski, White Plains, NY (US)

(73) Assignees: International Business Machines Corporation, Armonk, NY (US); Egypt Nanotechnology Center (EG)

( * ) Notice: Subject to any disclaimer, the term of this patent is extended or adjusted under 35 U.S.C. 154(b) by 259 days.

(21) Appl. No.: 12/886,908

(22) Filed: Sep. 21, 2010

(65) Prior Publication Data
US 2012/0069338 A1 Mar. 22, 2012

(51) Int. Cl.
*G01N 21/00* (2006.01)
*G01J 3/42* (2006.01)

(52) U.S. Cl. .......... 356/432; 356/319; 356/445; 257/24; 438/49

(58) Field of Classification Search .......... 356/300, 356/319, 326, 445–448, 432–440; 427/195.1, 427/532, 534, 122; 438/758, 49; 257/24
See application file for complete search history.

(56) References Cited

U.S. PATENT DOCUMENTS

| 5,306,644 | A * | 4/1994 | Myerholtz et al. ............. 436/149 |
|---|---|---|---|
| 5,527,711 | A * | 6/1996 | Tom-Moy et al. ............. 436/518 |
| 6,919,730 | B2 | 7/2005 | Cole et al. |
| 7,449,133 | B2 | 11/2008 | Gruner et al. |
| 7,670,831 | B2 | 3/2010 | Lee et al. |
| 2008/0212102 | A1* | 9/2008 | Nuzzo et al. ................. 356/445 |
| 2008/0219616 | A1* | 9/2008 | Wimberger-Friedl et al. . 385/12 |
| 2009/0235721 | A1 | 9/2009 | Robinson et al. |
| 2010/0021708 | A1 | 1/2010 | Kong et al. |
| 2010/0127312 | A1* | 5/2010 | Grebel et al. ................. 257/288 |
| 2010/0327847 | A1* | 12/2010 | Leiber et al. ................. 324/71.1 |
| 2011/0227043 | A1* | 9/2011 | Guo et al. ....................... 257/24 |
| 2011/0285999 | A1* | 11/2011 | Kim et al. ...................... 356/445 |
| 2011/0303899 | A1* | 12/2011 | Padhi et al. ..................... 257/29 |
| 2012/0003438 | A1* | 1/2012 | Appleton et al. ........... 428/195.1 |
| 2012/0063033 | A1* | 3/2012 | Gurney et al. ............. 360/234.3 |

FOREIGN PATENT DOCUMENTS
WO   WO2009157739   12/2009

OTHER PUBLICATIONS

T. Eberlin et al., Plasmon spectroscopy of free-standing graphene films, Physical Review B, 2008, pp. 233-406, vol. 77, The American Physical Society.
J. Homola et al., Present and future of surface plasmon resonance biosensors, Analytical and Bioanalytical Chemistry, 2003, pp. 528-539, vol. 377, Institute of Radio Engineering and Electronics, Academy of Sciences of the Czech Republic.
J. Zhao et al., Localized surface plasmon resonance biosensors, Nanomedicine, 2006, pp. 219-228, vol. 1, Future Medicine Ltd.
T. Neumann et al., Surface Plasmon Fluorescence Sectroscopy, Advanced Functional Materials, Sep. 9, 2002, pp. 575-586, vol. 12, Wiley-VCH.

* cited by examiner

*Primary Examiner* — Hoa Pham
(74) *Attorney, Agent, or Firm* — Cantor Colburn LLP; Vazken Alexanian

(57) ABSTRACT

A method of using an optical sensor, the optical sensor comprising a sensing surface comprising graphene layer, the sensing surface located on a substrate, includes determining a first optical absorption spectrum for the graphene layer by a spectrophotometer; adding an analyte, the analyte selected to cause a shift in the first optical absorption spectrum, to the graphene layer; determining a second optical absorption spectrum for the modified graphene layer by a spectrophotometer; determining a shift between the first optical absorption spectrum and the second optical absorption spectrum; and determining a makeup of the analyte based on the determined shift.

18 Claims, 4 Drawing Sheets

GRAPHENE OPTICAL SENSOR

FIELD

This disclosure relates generally to the field of optical sensors, and more particularly to a graphene optical sensor.

DESCRIPTION OF RELATED ART

Graphene refers to a two-dimensional planar sheet of carbon atoms arranged in a hexagonal benzene-ring structure. A free-standing graphene structure is theoretically stable only in a two-dimensional space, which implies that a truly planar graphene structure does not exist in a three-dimensional space, being unstable with respect to formation of curved structures such as soot, fullerenes, nanotubes or buckled two dimensional structures. However, a two-dimensional graphene structure may be stable when supported on a substrate, for example, on the surface of a silicon carbide (SiC) crystal. Free standing graphene films have also been produced, but they may not have the idealized flat geometry.

Structurally, graphene has hybrid orbitals formed by $sp^2$ hybridization. In the $sp^2$ hybridization, the 2s orbital and two of the three 2p orbitals mix to form three $sp^2$ orbitals. The one remaining p-orbital forms a pi ($\pi$)-bond between the carbon atoms. Similar to the structure of benzene, the structure of graphene has a conjugated ring of the p-orbitals, i.e., the graphene structure is aromatic. Unlike other allotropes of carbon such as diamond, amorphous carbon, carbon nano foam, or fullerenes, graphene is only one atomic layer thin.

Graphene has an unusual band structure in which conical electron and hole pockets meet only at the K-points of the Brillouin zone in momentum space. The energy of the charge carriers, i.e., electrons or holes, has a linear dependence on the momentum of the carriers. As a consequence, the carriers behave as relativistic Dirac-Fermions with a zero effective mass and are governed by Dirac's equation. Graphene sheets may have a large carrier mobility of greater than 200,000 $cm^2$/V-sec at 4K. Even at 300K, the carrier mobility can be as high as 15,000 $cm^2$V-sec.

Graphene layers may be grown by solid-state graphitization, i.e., by sublimating silicon atoms from a surface of a silicon carbide crystal, such as the (0001) surface. At about 1,150° C., a complex pattern of surface reconstruction begins to appear at an initial stage of graphitization. Typically, a higher temperature is needed to form a graphene layer. Graphene layers on another material are also known in the art. For example, single or several layers of graphene may be formed on a metal surface, such as copper and nickel, by chemical deposition of carbon atoms from a carbon-rich precursor.

Graphene displays many other advantageous electrical properties such as electronic coherence at near room temperature and quantum interference effects. Ballistic transport properties in small scale structures are also expected in graphene layers.

While single-layer graphene sheet has a zero band-gap with linear energy-momentum relation for carriers, two-layer graphene, i.e. bi-layer graphene, exhibits drastically different electronic properties, in which a band gap may be created under special conditions. In a bi-layer graphene, two graphene sheets are stacked on each other with a normal stacking distance of roughly 3.35 angstrom, and the second layer is rotated with respect to the first layer by 60 degree. This stacking structure is the so-called A-B Bernel stacking, and is also the graphene structure found in natural graphite. Similar to single-layer graphene, bi-layer graphene has zero-band gap in its natural state. However, by subjecting the bi-layer graphene to an electric field, a charge imbalance can be induced between the two layers, and this will lead to a different band structure with a band gap proportional to the charge imbalance.

SUMMARY

In one aspect, an optical sensor includes a substrate; and a sensing surface comprising a graphene layer located on the substrate, wherein the graphene layer is chemically modified with an analyte-specific binding substance.

In one aspect, a method of using an optical sensor, the optical sensor comprising a sensing surface comprising a graphene layer, the sensing surface located on a substrate, includes determining a first optical absorption spectrum for the graphene layer by a spectrophotometer; adding an analyte, the analyte selected to cause a shift in the first optical absorption spectrum, to the graphene layer; determining a second optical absorption spectrum for the modified graphene layer by a spectrophotometer; determining a shift between the first optical absorption spectrum and the second optical absorption spectrum; and determining a makeup of the analyte based on the determined shift.

In one aspect, a method of making an optical sensor includes forming a sensing surface comprising a graphene layer; transferring the graphene layer to a substrate; and chemically modifying the graphene layer with an analyte-specific binding substance.

Additional features are realized through the techniques of the present exemplary embodiment. Other embodiments are described in detail herein and are considered a part of what is claimed. For a better understanding of the features of the exemplary embodiment, refer to the description and to the drawings.

BRIEF DESCRIPTION OF THE SEVERAL VIEWS OF THE DRAWINGS

Referring now to the drawings wherein like elements are numbered alike in the several FIGURES.

DETAILED DESCRIPTION

Embodiments of a graphene optical sensor and methods of using a graphene optical sensor are provided, with exemplary embodiments being discussed below in detail. Operation of an optical sensor may be based on detection of a shift in a peak resonance frequency of surface plasmons (i.e., collective oscillations of electrons) on a sensing surface in the presence of an analyte. Surface plasmons may be excited on a sensing surface, which may include a noble metal such as silver or gold, using polarized light in total internal reflection (TIR) mode. The peak plasmon resonance of the sensing surface may be observed by measuring the optical absorption spectrum of the sensing surface using a spectrophotometer. Graphene is a semi-metal material on which surface plasmons may be excited, and is also transparent. Therefore, an optical sensor that utilizes graphene as the sensing surface may be used in both TIR and transmission mode, unlike an optical sensor that uses a metal for the sensing surface.

A graphene optical sensor may be used to determine the makeup of any analyte that acts to shift the peak surface plasmon resonance (SPR) of the graphene. Some exemplary sensing applications appropriate for a graphene optical sensor include, but are not limited to, a chemical sensor for chemicals such as explosives, an environmental sensor for pollutants, or a biosensor for detecting biomolecules, such as DNA, viruses, or protein interactions. The graphene sensing surface may be modified with a compound for binding specific biomolecules contained in the analyte in some embodiments. The graphene surface may also be modified with analytes including different surface moieties, allowing for the analysis of multiple analytes at once. A patterned graphene sensing surface may be dipped into an analyte solution, removed and then scanned to test for multiple analyte components at once.

Surface plasmons on unmodified graphene are excited at a peak wavelength of about 267 nanometers (nm). The charge carriers in graphene may be increased by doping, allowing adjustment of the peak wavelength of the graphene, resulting in a surface plasmon wave that may be generated upon absorption of light of a specific wavelength. Exposure of graphene to a plasma may also adjust the optical absorption peak of the graphene. The plasmon peak of a particular graphene layer may be determined by measuring the absorption spectrum of the graphene using a spectrophotometer. After the absorption spectrum and peak wavelength of the graphene layer are determined, the graphene surface may be modified by addition of an analyte that includes, for example, a chemical or a biological material. Then, by measuring the absorption spectrum of the graphene in the presence of the analyte, a shift in the plasmon peak of the graphene in the presence of the analyte may be determined, and a makeup of the analyte may be determined from the shift.

Figure 1:
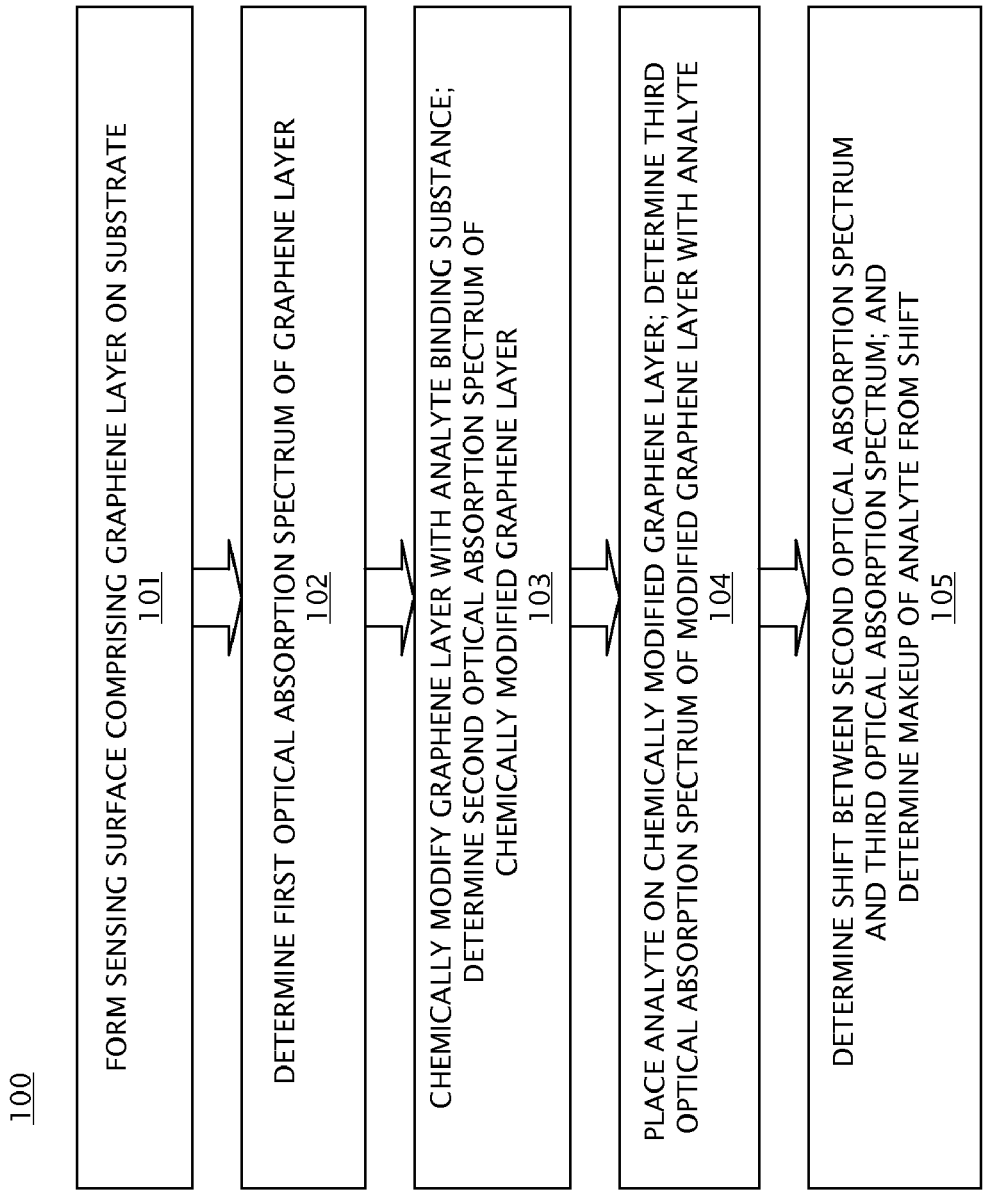
FIG. 1 illustrates an embodiment of a method of using a graphene optical sensor.
Figure 2:
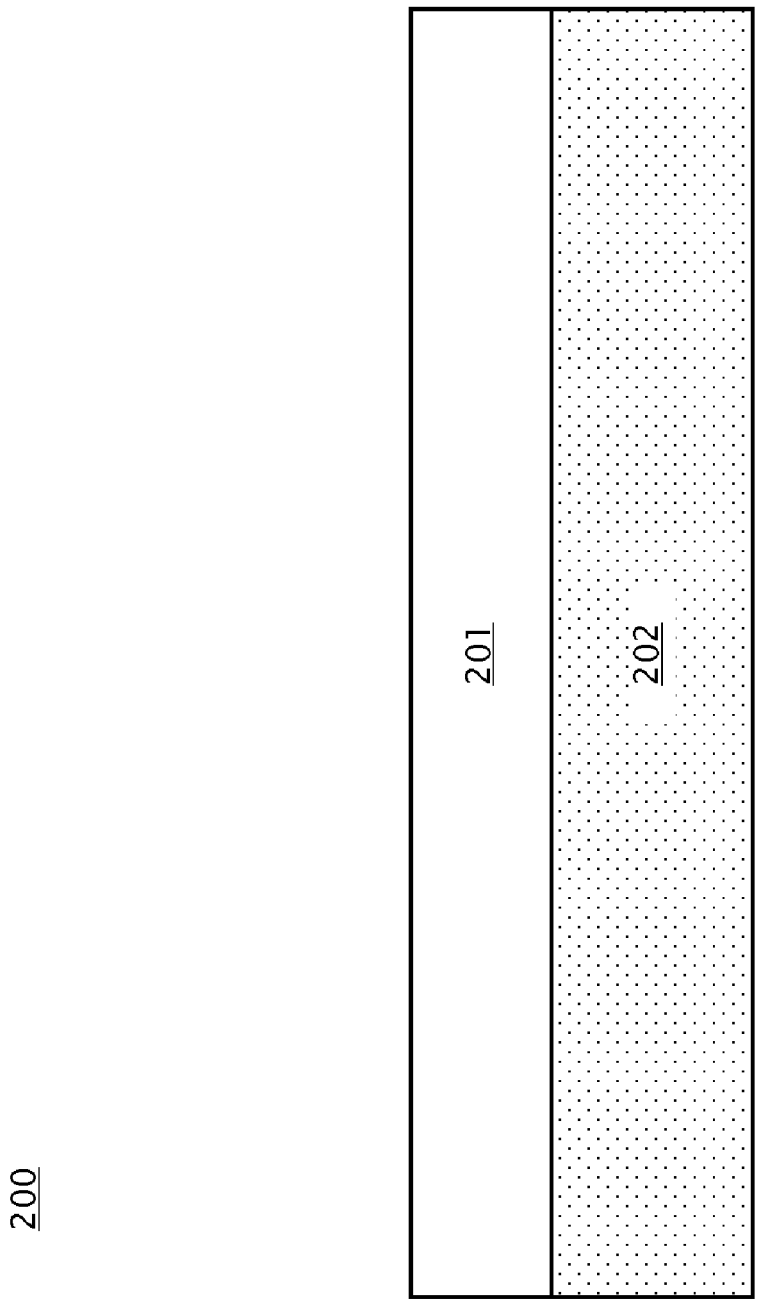
FIG. 2 illustrates an embodiment of a graphene optical sensor.

FIG. 1 illustrates an embodiment of a method of using a graphene optical sensor. FIG. 1 is discussed with respect to FIGS. 2-4. In block 101, a graphene optical sensor is formed by forming a sensing surface comprising a graphene layer on a substrate. FIG. 2 illustrates an embodiment of an optical sensor 200, including graphene layer 201 on substrate 202. Graphene layer 201 may be a single layer of graphene in some embodiments, or a multilayer of graphene in other embodiments. The graphene layer 201 may be formed separately and then transferred to the substrate 202 in some embodiments, or may be formed directly on the substrate 202 in other embodiments. The graphene layer 201 may be formed by any appropriate method, including but not limited to chemical vapor deposition (CVD), mechanical exfoliation, adhesion, chemical exfoliation, or thermal decomposition of silicon carbide (SiC). The graphene layer 201 may include a network or film of graphene flakes in some embodiments. Substrate 202 may comprise any appropriate material, depending on the mode in which sensor 200 is used. For a graphene optical sensor 200 used in transmission mode (discussed below with respect to FIG. 3), the substrate 202 may be a material that is transparent in the approximate frequency range of the absorption peak of graphene layer 201, including but not limited to quartz, glass, or sapphire. For a graphene optical sensor 200 that is used in TIR mode (discussed below with respect to FIG. 4), the substrate 202 may be any appropriate material, including but not limited to an opaque material such as gold or silver. The graphene layer 201 may be doped or exposed to a plasma to adjust the peak absorption wavelength of the graphene layer 201 in some embodiments.

Figure 3:
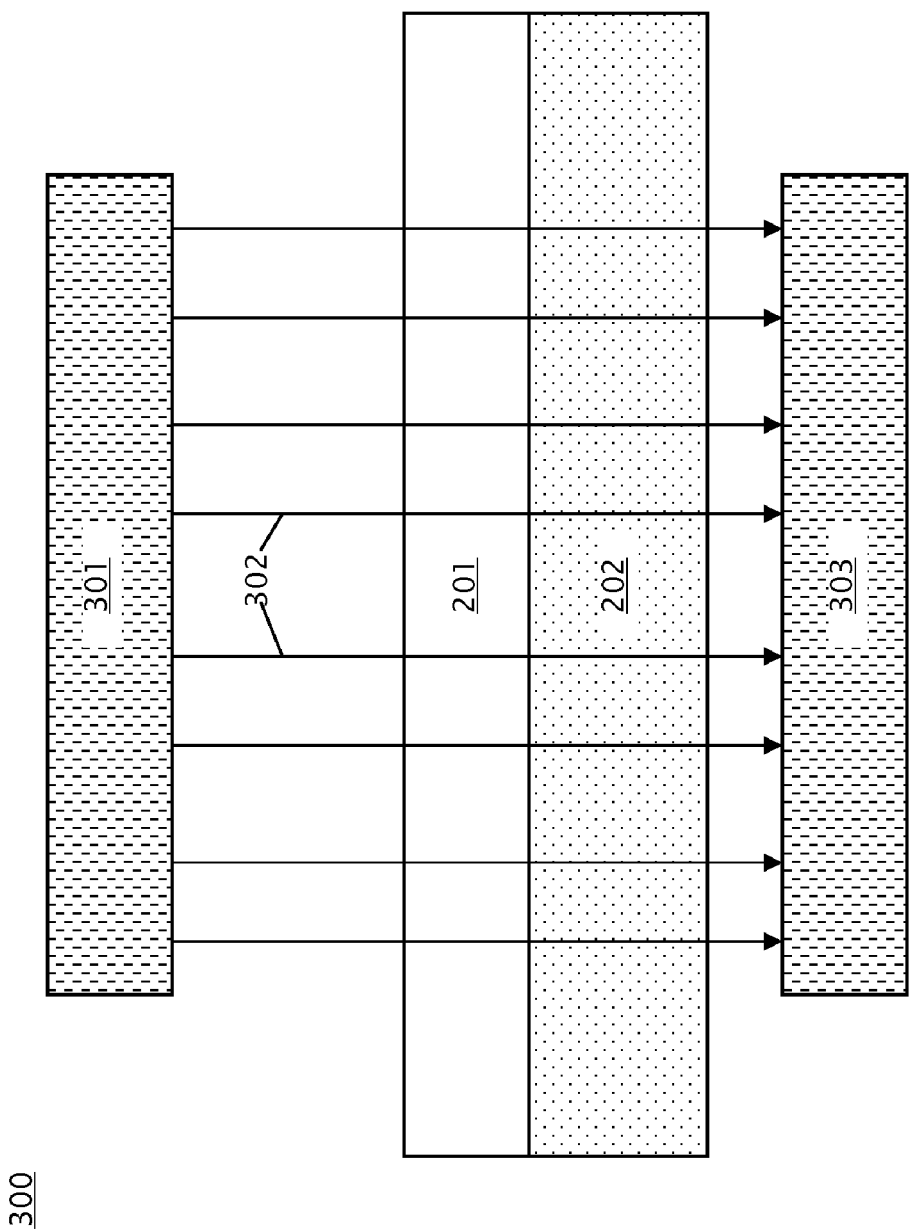
FIG. 3 illustrates an embodiment of a graphene optical sensor in transmission mode.
Figure 4:
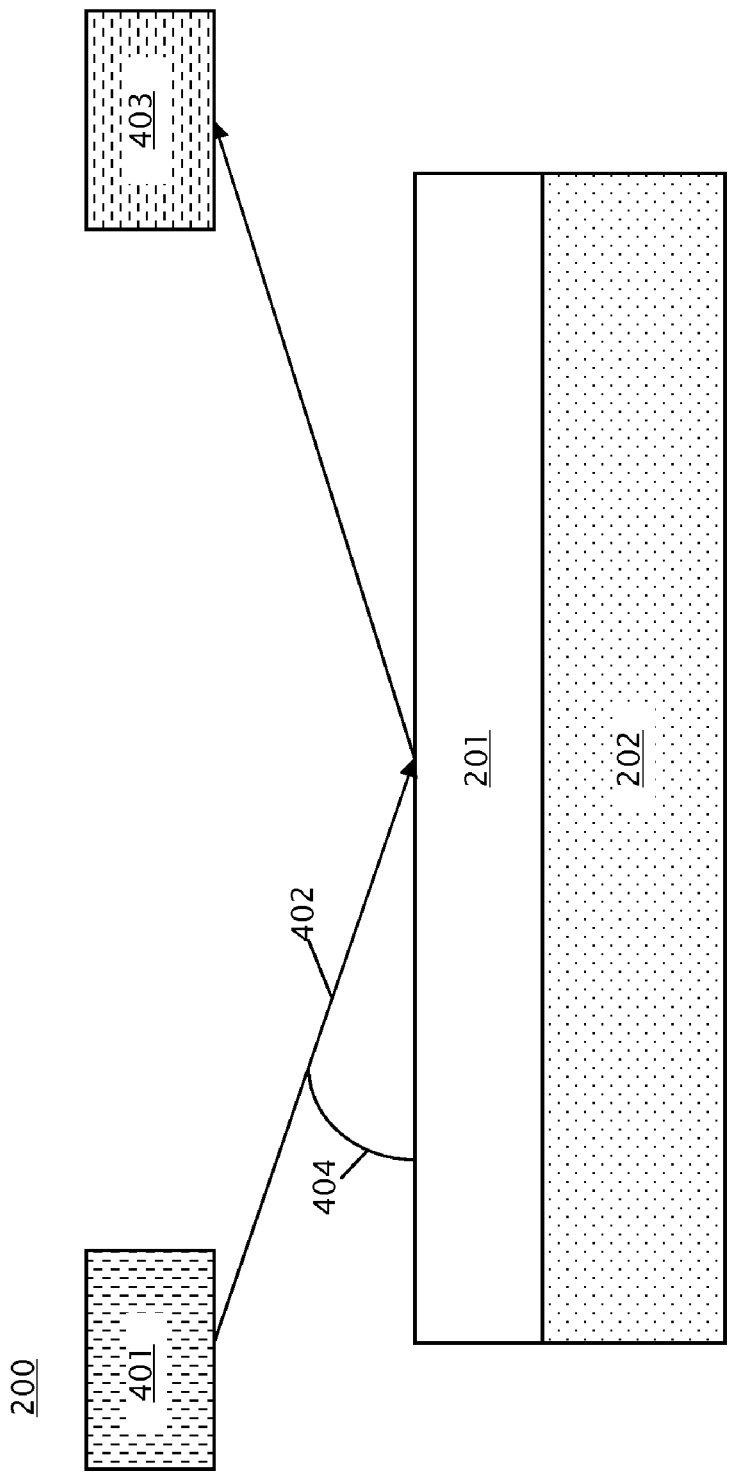
FIG. 4 illustrates an embodiment of a graphene optical sensor in total internal reflection (TIR) mode.

In block 102, a first optical absorption spectrum for the unmodified graphene layer 201 is determined. The optical absorption spectrum may be determined in transmission mode, as illustrated in FIG. 3, or in TIR mode, as illustrated in FIG. 4. FIG. 3 illustrates an embodiment 300 of a graphene optical sensor in transmission mode. In transmission mode, a spectrophotometer transmitter 301 is used to transmit optical energy 302 through the graphene layer 201 and substrate 202 to spectrophotometer receiver 303. The graphene layer 201 absorbs a portion of optical energy 302, allowing spectrophotometer receiver 303 to determine an optical absorption spectrum for the graphene layer 201. A peak absorption wavelength for graphene layer 201 may then be determined from the optical absorption spectrum. In TIR mode, as shown in FIG. 4, the spectrophotometer transmitter 401 transmits the optical energy 402 at an angle to graphene layer 201, and a reflected portion of the optical energy 402 is received at spectrophotometer receiver 403. As angle 404 is modified, the amount of optical energy reflected from the surface of graphene layer 201 to spectrophotometer receiver 403 changes, allowing determination of the optical absorption spectrum of the graphene 201. The angle 404 at which all of the optical energy is reflected from the surface of graphene layer 201 to spectrophotometer receiver 303 indicates the peak absorption wavelength of the graphene layer 201.

In block 103, the graphene layer 201 is chemically modified by the addition of an analyte-specific binding substance to the surface of the graphene layer 201, and a second optical absorption spectrum for the chemically modified graphene layer 201 is determined. The chemical modification of graphene layer 201 may be covalent or non-covalent, depending on the type of analyte for which graphene sensor 200 is to be used. The analyte-specific binding substance on graphene layer 201 may be a molecule that specifically binds to a biomolecule in the analyte or to a chemical agent to be detected in the analyte. Chemical modification of the graphene layer 201 with the analyte-specific binding substance in block 103 makes the sensor 200 a specific sensor for one type of analyte. The second optical absorption spectrum of the modified graphene layer 201 may be determined by a spectrophotometer in either transmission mode or in TIR mode, as discussed above with respect to FIGS. 3 and 4, respectively. A second peak absorption for the modified graphene layer may be determined from the second optical absorption spectrum.

In block 104, an analyte is placed on the surface of graphene layer 201, and a third optical absorption spectrum for the graphene layer 201 in the presence of the analyte is determined. The analyte binds to the analyte-specific binding substance that was added to the graphene layer 201 in block 103, and causes a shift in the absorption spectrum of the graphene layer 201. The analyte may include any material that will cause a shift in the optical absorption spectrum of the graphene 201. The analyte may include a chemical, such as an explosive; an environmental pollutant, or biomolecules, such as DNA, viruses, or proteins. The third optical absorption spectrum of the graphene layer and analyte may be determined by a spectrophotometer in either transmission mode or in TIR mode, as discussed above with respect to FIGS. 3 and 4, respectively. A third peak absorption for the modified graphene layer in the presence of the analyte may be determined from the third optical absorption spectrum.

In block 105, a shift between the second optical absorption spectrum that was determined in block 103 and the third optical absorption spectrum that was determined in block 104 is determined, and the shift is used to determine a makeup of the analyte. Determination of the makeup of the analyte may include determining an amount of a material (such as a chemical or biomolecule) that is present in the analyte.

The technical effects and benefits of exemplary embodiments include an optical sensor that may be used in both TIR and transmission mode.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. An optical sensor, comprising:
    a substrate;
    a sensing surface comprising a graphene layer located on the substrate, wherein the graphene layer is chemically modified with an analyte-specific binding substance; and
    an analyte located on the chemically modified graphene layer, wherein the analyte is selected to cause a shift in an optical absorption spectrum of the chemically modified graphene layer.

2. The optical sensor of claim 1, further comprising a spectrophotometer configured to determine an optical absorption spectrum for the graphene layer in a total internal reflection mode.

3. The optical sensor of claim 1, further comprising a spectrophotometer configured to determine an optical absorption spectrum for the graphene layer in a transmission mode.

4. The optical sensor of claim 1, wherein the analyte binds to the analyte-specific binding substance.

5. The optical sensor of claim 1, wherein the analyte comprises one of a biomolecule and a chemical.

6. The optical sensor of claim 1, wherein the substrate comprises a transparent material, and wherein the optical sensor is configured to be used in a transmission mode.

7. The optical sensor of claim 1, wherein the substrate comprises an opaque material, and wherein the optical sensor is configured to be used in a total internal reflection mode.

8. An optical sensor, comprising:
    a substrate; and
    a sensing surface comprising a graphene layer located on the substrate, wherein the graphene layer is chemically modified with an analyte-specific binding substance, and is doped to adjust an optical absorption spectrum of the graphene layer.

9. The optical sensor of claim 8, wherein the transparent material comprises one of quartz, sapphire, and glass.

10. A method of using an optical sensor, the optical sensor comprising a sensing surface comprising graphene layer, the sensing surface located on a substrate, the method comprising:
    determining a first optical absorption spectrum for the graphene layer by a spectrophotometer;
    adding an analyte, the analyte selected to cause a shift in the first optical absorption spectrum, to the graphene layer;
    determining a second optical absorption spectrum for the modified graphene layer by a spectrophotometer;
    determining a shift between the first optical absorption spectrum and the second optical absorption spectrum; and
    determining a makeup of the analyte based on the determined shift.

11. The method of claim 10, wherein the substrate comprises a transparent material.

12. The method of claim 11, wherein the transparent material comprises quartz.

13. The method of claim 10, wherein determining the first optical absorption spectrum and second optical absorption spectrum for the graphene layer by a spectrophotometer comprises operating the spectrophotometer in a transmission mode.

14. The method of claim 10, further comprising chemically modifying the graphene layer with an analyte-specific binding substance before determining the first optical absorption spectrum.

15. A method of making an optical sensor, the method comprising:
    forming a sensing surface comprising a graphene layer;
    transferring the graphene layer to a substrate;
    chemically modifying the graphene layer with an analyte-specific binding substance; and
    doping the graphene layer to adjust an optical absorption spectrum of the graphene layer.

16. The method of claim 15, wherein the substrate comprises a transparent material.

17. The method of claim 16, wherein the transparent material comprises quartz.

18. The method of claim 15, wherein the analyte-specific binding substance is configured to bind to an analyte placed on the graphene layer.

* * * * *